United States Patent [19]

Ollar

[11] Patent Number: 5,153,119
[45] Date of Patent: Oct. 6, 1992

[54] METHOD FOR SPECIATING AND IDENTIFYING MAI (MYCOBACTERIUM AVIUM-INTRACELLULARE)

[75] Inventor: Robert-A. Ollar, Brooklyn, N.Y.

[73] Assignee: Infectech Inc., Milford, Pa.

[21] Appl. No.: 426,573

[22] Filed: Oct. 24, 1989

[51] Int. Cl.$^5$ .......................... C12Q 1/04; C12N 1/00
[52] U.S. Cl. ........................................ 435/34; 435/29; 435/30; 435/864
[58] Field of Search ..................... 435/864, 29, 30, 34

[56] References Cited

PUBLICATIONS

O'Hara et al J Clinical Microbiology vol. 27, No. 9 pp. 2046-2049.
Poropatich et al J Clinical Microbiology vol. 25, No. 5 pp. 929-930.
Warren et al J Clinical Microbiology vol. 18, No. 1 pp. 546-549.
Resnick et al. Biol Abst. 86(8) Abstract #77742 1989.
Cox et al Biol Abst 65(10) Abstract #59630 1978.
Wallace, J. M. et al., "*Mycobacterium avium* Complex in Patients with Acquired Immunodeficiency Syndrome—A Clinicopathologic Study", Chest, 93(5): 926-932 (1988).
Gonzalez, R. et al., "Evaluation of Gen-Probe DNA Hybridization Systems for the Identification of *Mycobacterium tuberculosis* and *Mycobacterium avium-intracellulare*", Diagnosis Microbiology Infect. Dis., 8:69-77 (1987).
Mishra, S. K. et al., "Observations On Paraffin Baiting As a Laboratory Diagnostic Procedure in Nocardiosis", Mycopathologica and Mycologia Applicata 51 (2-3): 147-157 (1973).
Ollar, R. A., "A Paraffin Baiting Technique that Enables a Direct Microscopic view of in situ Morphology of *Nocardia asteroides* with the Acid-Fast or Fluorescence Staining Procedures", Zbl. Bakt. Hyg., Abt. Orig. A, 234: 81-90 (1976).
Singh, M. et al., "Comparison of Paraffin Baiting and Conventional Culture Techniques for Isolation of *Nocardia asteroides* from Sputum, Journal of Clinical Microbiology", Jan. 1987, pp. 176-177.

Primary Examiner—Douglas W. Robinson
Assistant Examiner—Jane A. Williams
Attorney, Agent, or Firm—Arnold B. Silverman; David V. Radack

[57] ABSTRACT

A method of speciating and identifying MAI in a specimen comprises placing a paraffin coated slide in a receptacle containing a sterile aqueous solution inoculated with the specimen, analyzing the slide after exposure to the specimen to determine the presence or absence of atypical Mycobacteria, and after the analysis step, if atypical Mycobacteria are determined to be present, performing at least one speciation assay to ascertain if the atypical Mycobacteria are MAI. A related apparatus is also disclosed for speciating and identifying MAI in a specimen comprising a paraffin-wax coated slide, a tube having a sterile aqueous solution contained therein, the tube adapted to hold the slide, and at least one speciation assay means for performing an assay to determine the presence or absence of MAI in the specimen after the specimen is introduced into the tube holding the solution and the slide. An apparatus and method for determining the sensitivity of MAI to different antibiotics and dosages thereof is also provided.

15 Claims, 2 Drawing Sheets

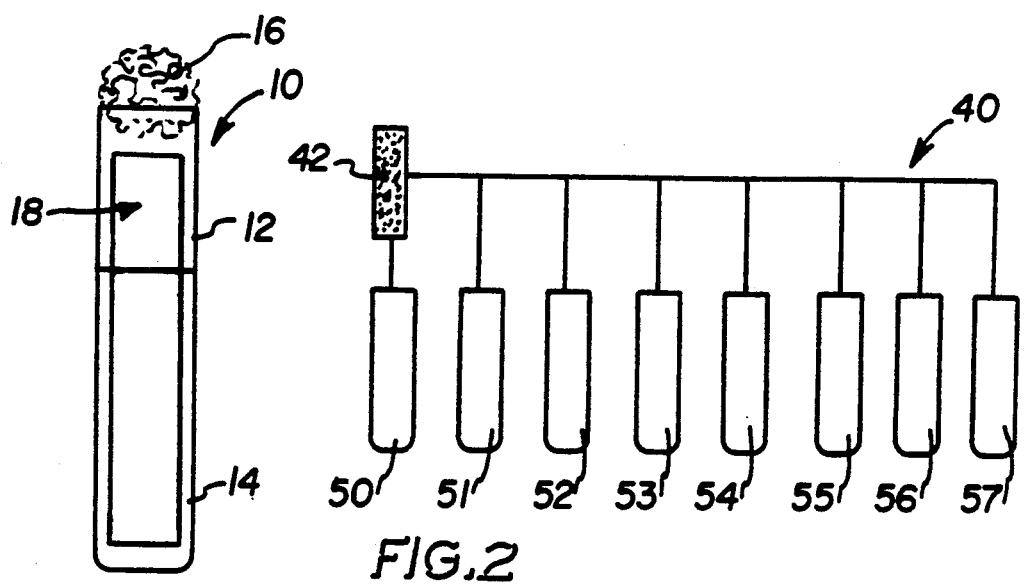
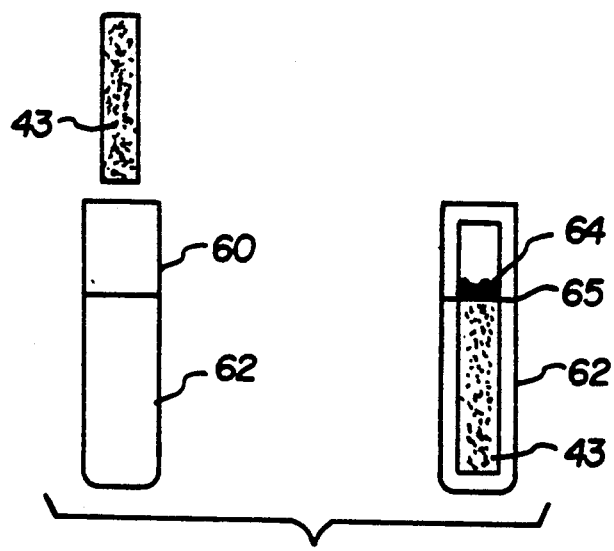
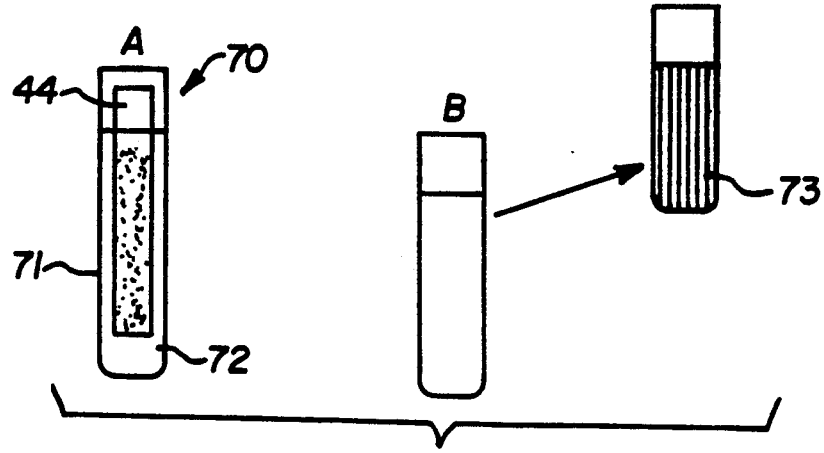

METHOD FOR SPECIATING AND IDENTIFYING MAI (MYCOBACTERIUM AVIUM-INTRACELLULARE)

BACKGROUND OF THE INVENTION

1. Field of the Invention

This invention relates to a method and apparatus for speciating and identifying *Mycobacteria avium-intracellulare* complex ("MAI"), and testing the same for antibiotic sensitivity and more particularly to a method and apparatus for determining the presence or absence of atypical Mycobacteria (mycobacteria other than *M. tuberculosis*, *M. leprae*, and *M. paratuberculosis*) and nocardioform organisms and that ultimately speciates and identifies MAI.

2. Description of the Prior Art

Human immunodeficiency virus type 1 or HIV causes acquired immunodeficiency syndrome ("AIDS") which is a fatal disease approaching epidemic proportions throughout the world. By current estimates, about 15-34% of infected individuals will probably develop AIDS within 3-5 years. During the asymptomatic stage of AIDS, although most patients have no symptoms, some patients a few weeks after exposure develop a disorder resembling mononucleosis. Later, its symptoms include fatigue, fever and swollen glands, diarrhea and minor infections. Most of these symptoms disappear initially, but may recur. When AIDS develops, it is usually characterized by a major opportunistic infection, such as *Pneumocystis pneumonia*, or an opportunistic tumor, such as Kaposi's sarcoma or a lymphoma. At this stage, the disease is uniformly fatal.

It has been found that more than 50% of the AIDS patients have MAI present in their bodies. Wallace, J. M. and Hannah, J. B., "*Mycobacterium avium* Complex in Patients with Acquired Immunodeficiency Syndrome-A Clinicopathologic Study", Chest 93(5): 926-932 (1988). The MAI complex infection in AIDS patients has been shown to be widely disseminated in the patient, however the most common source of isolation is in the blood. There is currently no effective treatment against MAI as these organisms are often resistant to standard therapy.

It is known to use isolation techniques for determining the presence or absence of MAI in the patient's blood. One method involves using the BACTEC Radiometric System, which is a product of the Johnston Division of Becton and Dickenson. The system itself utilizes hemoculture tubes that contain Middlebrook 7H12 liquid broth plus 0.05% (v/v) sodium polyanethyl sulphonate in hemoculture vials. In addition, the 7H12 broth contains Carbon-14 labelled palmitic acid. In use, vials containing mycobacterial growth give off Carbon-14 labelled $CO_2$ and this is detected by a device similar to that used for liquid scintillation counter capable of detecting beta emitters. See Kirihara, J. M. et al. "Improved Detection Times for *Mycobacterium avium* Complex and *Mycobacterium tuberculosis* with BACTEC Radiometric System", J. Clin. Microbiol. 22:841-845 (1985).

Another method of isolation involves using genetic probes which rely upon DNA hybridization. Gonzalez, R. et al., "Evaluation of Gen-Probe DNA Hybridization Systems for the Identification of *Mycobacterium tuberculosis* and *Mycobacterium avium-intracellulare* Diagnosis", Microbiology Infect. Dis. 8:69-77 (1987).

These known methods, although effective, require expensive equipment and specialized operating personnel and materials Thus, smaller hospital centers where few AIDS patients are seen, field laboratories, and third world countries, where resources are limited, do not have this specialized equipment and personnel. A simpler and more inexpensive method and apparatus of isolating and identifying MAI would be of substantial benefit in such situations.

It is known that many atypical Mycobacteria grow on basal salt media devoid of any carbon sources other than paraffin-wax which is introduced into the media in the form of paraffin-wax coated rods. Fuhs, G. W., "Der Mikrobielle Abbau Von Kohlenwasserstoffen", Arch. Mikrobiol. 39:374-422 (1961). Mishra, S. K. et al., "Observations On Paraffin Baiting As a Laboratory Diagnostic Procedure in Nocardiosis", Mycopathologica and Mycologia Applicata 51 (2-3):147-157 (1973) utilized paraffin coated rods and basal salt medium to isolate *Nocardia asteroides* from clinical specimens such as sputum, bronchial lavage and cerebrospinal fluid.

The technique was further improved by substituting paraffin-wax coated slides for rods and thereby making possible the use on an in situ Kinyoun cold acid-fastness staining procedure for organisms growing on the paraffin coated slide. Ollar, R. A., "A Paraffin Baiting Technique that Enables a Direct Microscopic View of "in situ" Morphology of *Nocardia asteroides* with the Acid-Fast or Fluorescence Staining Procedures", Zbl. Bakt. Hyg., Abt. Orig. A, 234:81-90 (1976). With this assay, a positive reaction tells the user immediately that a mycobacteria organism other than *M. tuberculosis* is present.

Despite the above teachings, however, there still remains a need for efficient and economical method and an inexpensive apparatus for identification and speciating of MAI.

SUMMARY OF THE INVENTION

The present invention has met the above-described needs. The method of speciating and identifying MAI in a specimen comprises placing a paraffin coated slide in a receptacle containing a sterile aqueous solution inoculated with the specimen, analyzing the slide after exposure to the specimen to determine the presence or absence of atypical Mycobacteria, and after the analysis step, if atypical Mycobacteria are determined to be present, performing at least one speciation assay to ascertain if the atypical Mycobacteria are MAI. A related apparatus is also provided for speciating and identifying MAI in a specimen comprising a paraffin-wax coated slide, a tube having a sterile aqueous solution contained therein, the tube adapted to hold the slide, and at least one speciation assay means for performing an assay to determine the presence or absence of MAI in the specimen after the specimen is introduced into the tube holding the solution and the slide.

An apparatus and method for determining the sensitivity of MAI to different antibiotics and dosages thereof is also provided. The apparatus comprises a plurality of test tubes each adapted to contain a sterile aqueous broth, an amount of antibiotic to be tested and MAI complex organisms to be assayed, and a plurality of paraffin coated slide cultures which have been exposed to a specimen containing MAI complex organisms plus antibiotic in the test tubes. Observing growth of the MAI complex organisms on the slides can be used to determine the concentration of the antibiotic necessary to resist the MAI complex organism growth on the slide. The method comprises providing a plurality of test tubes each containing sterile aqueous broth, an amount of antibiotic to be tested, and MAI complex organisms assayed, incubating the test tubes and observing the MAI complex organism growth on the slides at discrete time intervals. In this way, the minimum inhibitory concentration of the antibiotic necessary to resist the MAI complex organism growth on the slide can be determined.

It is an object of the invention to identify and speciate MAI by a method that is simple and efficient.

It is a further object of the invention to provide an MAI identification apparatus that is inexpensive and easy to use.

It is a further object of the invention to provide an MAI identification apparatus that does not require specialized training for a person to operate.

It is a further object of the invention to provide for a plurality of different tests to determine the presence or absence of MAI in a specimen.

It is a further object of the invention to provide a method that reduces the risk of contamination.

It is a further object of the invention to provide a method and apparatus for testing the sensitivity of antibiotics to the MAI organism.

These and other objects will be more fully understood with reference to the description and to the drawings appended to this application.

BRIEF DESCRIPTION OF THE DRAWINGS

FIG. 1 shows a schematic front elevational view of a test tube holding the paraffin coated slide in a sterile aqueous solution inoculated with MAI.

FIG. 2 shows a schematic view of the acid-alcohol fastness assay.

FIG. 3 shows the tellurite reduction assay.

FIG. 4 shows the nitrate reduction assay.

DESCRIPTION OF THE PREFERRED EMBODIMENTS

Figure 5:
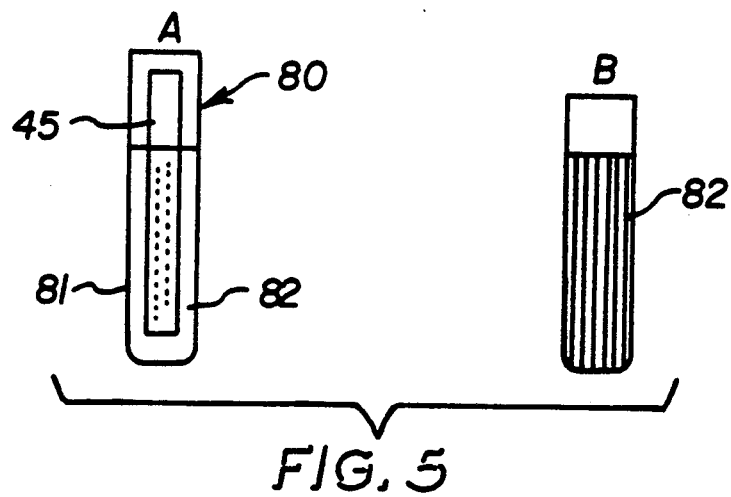
FIG. 5 shows the urea hydrolysis assay.

When referred to herein, the term "atypical Mycobacteria" means all mycobacteria other than *M. tuberculosis, M. leprae,* and *M. paratuberculosis.*

Referring to FIG. 1, part of the MAI isolation and speciation kit 10 is shown. FIG. 1 shows a standard test tube 12 which contains a sterile aqueous solution 14 (such as Czapek broth) and a cotton plug 16 to seal the tube 12. In use, the specimen to be tested for the presence or absence of MAI is introduced into the test tube 12 and the paraffin coated slide 18 is subsequently analyzed. The specimen can be an amount of a patient's blood, stool or sputum. The latter two specimens can be directly inoculated into the MAI isolation and speciation kit without the need for some sort of hemoculture broth.

Preferably, the slides 18 are prepared by first cutting standard microscope slides longitudinally so that they fit into the test tubes 12 and so they can be easily withdrawn. The test tubes 12 are plugged and sterilized by autoclaving.

The paraffin coating on the slides is preferably accomplished by first melting several tubes of sterilized histological grade paraffin embedding wax in a boiling water bath, while separately, a glass petri dish containing a slide support is heated on an electric hot plate to a temperature sufficient to keep the paraffin molten. The molten paraffin-wax is then poured into the heated petri dish to a level sufficient to cover a slide on the support.

Ethanol-flame sterilized forceps are preferably used to transfer a previously uncoated slide onto the slide support in the heated petri dish which contains the molten wax. The slide is immersed in the molten wax for a few seconds such that it is covered by a thin coat of paraffin-wax. A plurality of slides are prepared in this same fashion, with a tube of molten paraffin-wax added after 6-10 slides have been prepared to ensure that there is always sufficient wax to cover the supported slides.

The Czapek broth 14 can be provided with an antibacterial and antifungal/antibiotic cocktail such as that sold under the trade name "PANTA" made by Becton Dickenson/Johnston Labs Division. This product will resist possible contaminating factors such as *Pseudomonas aeruginosa* or *Candida tropicalis.* This product has no effect on the MAI since the MAI is resistant to the currently used antibiotics in "PANTA".

The kit 10 can also serve as a means of distinguishing between atypical Mycobacteria and nocardioform organisms on the one hand and *Mycobacterium tuberculosis* on the other hand because the latter cannot utilize paraffin-wax as a sole source of carbon. As is known, a tropism is created between the paraffin and organisms capable of using the paraffin as its carbon source, such as atypical Mycobacteria and nocardioform organisms. The outward manifestation of this tropism or baiting is the appearance of growth on the paraffin surface.

Once it is determined that a Mycobacteria other than *Mycobacteria tuberculosis* or a nocardioform organism is present on the slide, an alcohol-acid fastness test 40 (FIG. 2) can be used to further distinguish between the atypical Mycobacteria and the nocardioform organisms. As is known, atypical Mycobacteria are alcohol-acid fast; nocardioform organisms are acid-fast and *Pseudomonas aeruginosa* or *Candida tropicalis* are neither acid nor alcohol-acid fast. Thus, these latter two groups (nocardioforms and *Pseudomonas aeruginosa* or *Candida tropicalis*) can be eliminated as possibilities by the alcohol-acid fastness testing kit 40.

Referring to FIG. 2, the acid-alcohol fastness testing means 40 is shown. This testing means 40 includes a plurality of test tubes containing different solutions. The solutions stain the MAI on the slide for subsequent analysis under a microscope.

The paraffin coated slide culture with visible MAI growth 42 is removed from the test tube 12 of FIG. 1 and is first immersed in two consecutive tubes of distilled water 50, 51 and then immersed in a tube of Kinyoun carbolfuchsin 52 for fifteen minutes. The slide 42 is again immersed in a tube of distilled water 53 and then placed in a tube 54 containing acid-alcohol consisting of 97 ml absolute ethanol and 3.0 ml concentrated HCl for five minutes. After this, the slide is washed in a fourth tube of distilled water 55 and then placed into a tube 56 of 1.0% (v/v) aqueous Methylene blue solution for 1 minute. Finally, the slide is washed in a fifth tube 57 of distilled water.

The slide culture is then removed from the fifth tube 57 of distilled water and blotted gently with a clean absorbent paper tissue. The slide culture is then viewed under a microscope at 250×, 450× and 1000× oil immersion.

FIG. 3 shows the tellurite reduction assay which consists of a test tube 60 filled, preferably, with a Czapek broth plus an amount of potassium tellurite reagent 62. A cultured slide 43 is immersed into the test tube 60 and incubated. If MAI is present on the slide, a heavy black precipitate 64 forms at the level of the meniscus pellicle 65 of the slide 43. This test alerts the user to the possibility of MAI presence. MAI presence can be confirmed after the assay results are known for the assays discussed hereinafter.

FIG. 4 shows the nitrate reduction assay 70. A slide culture 44 showing heavy growth is assayed for the ability to reduce nitrates to nitrites. This is done by adding nitrates to a tube 71 containing a sterile broth. After a period of 12-24 hours incubation at 37° C., the slide 44 is removed from the sterile nitrate broth 72 and five drops of sulfanilic acid reagent solution followed by five drops of alpha naphthylamine reagent solution are added to the tubes 71. The reduction of nitrate to nitrite appears as a red colored broth 73. As is known, if the nitrate is reduced to nitrite, this indicates the absence of MAI on the slide.

FIG. 5 shows the urea hydrolysis reaction assay 80. A slide culture 45 is added to a plugged tube 81 containing 4.5 ml of sterile urea broth 82. The culture is incubated at 37° C. and checked after a period of three days. A positive reaction involves a color change of the broth 82 to pink or red after a period of three days. As is known, if the solution changes color, this indicates the absence of MAI on the slide 45.

Figure 6:
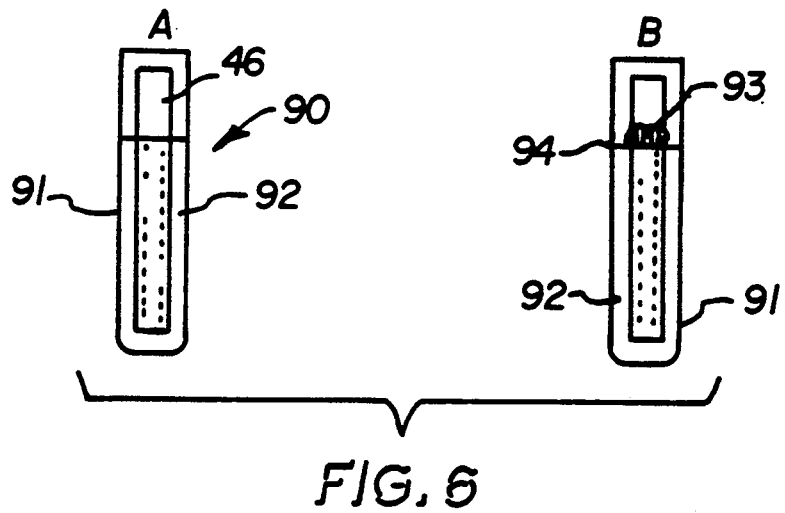
FIG. 6 shows the Tween 80 hydrolysis assay.

FIG. 6 shows the emulsifier hydrolysis assay 90. The emulsifier used is "Tween 80", a trademark of Atlas Chemical Industries, Inc. and is generically described as polyoxyethylene derivatives of fatty acid partial esters of sorbitol anhydrides. A slide culture 46 was added to sterile plugged tubes 91 containing Tween 80 media 92 and incubated at 37° C. A positive reaction involved the appearance of a red coloration 93 on the meniscus pellicle 94 of the slide 46 within five days. As is known, the presence of the red coloration in the slide indicates the absence of MAI on the slide.

It will be appreciated that at least one of the MAI identification tests (tellurite reduction, nitrate reduction, urea hydrolysis or "Tween 80" hydrolysis) should be performed, with the tellurite reduction test being the most important of the four tests. Preferably, all four of the tests should be performed in order to more accurately speciate and identify MAI.

Figure 7:
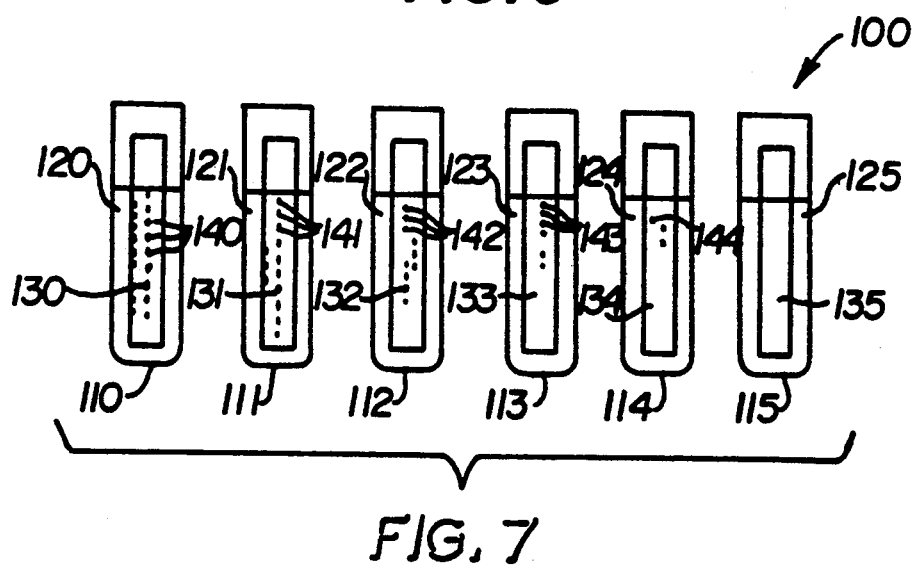
FIG. 7 shows the antibiotic sensitivity testing assay.

FIG. 7 shows the antibiotic sensitivity testing assay 100. This method and the associated apparatus tests the sensitivity of the MAI to different antibiotics and/or dosages of antibiotics. The assay consists of preferably six tubes 110-115 each containing an amount of Czapek broth solution 120-125. Broth solutions 121-125 contain uniform intervals of increasing concentration of an antibiotic to be tested. Broth 120 does not contain an amount of the antibiotic as this tube 110 will be the "control" tube. Tube 110, preferably, contains an amount of saline.

Paraffin slide cultures 130-135 were prepared as was discussed hereinbefore. Each of these slide cultures 130-135 are introduced into their respective tubes 110-115. The tubes 110-115 with slide cultures 130-135 are then incubated at 37° C. and checked at four days, seven days and eleven days. By observing the MAI growth 140-144 on the paraffin surfaces of each of the slide cultures 130-135, the minimal inhibitory concentration (MIC) of antibiotic necessary to prevent MAI growth on the paraffin culture slides 130-135 can be determined. In the case of FIG. 7, the MIC concentration is found in tube 115 because there is no MAI growth on slide 135.

It will be appreciated that the present invention provides a method and apparatus for identifying MAI and for testing the same for antibiotic sensitivity. The apparatus is easy to use and inexpensive and the method is accurate and efficient.

Whereas particular embodiments of the invention have been described hereinabove, for purposes of illustration, it will be evident to those skilled in the art that numerous variations of the details may be made without departing from the invention as defined in the appended claims.

I claim:

1. A method of determining the presence of *Mycobacterium avium-intracellulare* ("MAI") in a specimen comprising:
    placing one paraffin coated slide each in a plurality of separate receptacles, each receptacle containing a sterile aqueous solution inoculated with said specimen;
    observing said paraffin coated slides for the presence of organisms growing thereon;
    after observing organism growth on said paraffin coated slides, performing an alcohol-acid fastness test on a first said paraffin coated slide to determine whether said organism is an alcohol-acid fast organism, an acid-fast organism or a non-acid-fast/non-alcohol-fast organism;
    after performing said alcohol-acid fastness test on said first paraffin coated slide and determining that an alcohol-acid fast organism is present on said first paraffin coated slide, performing a tellurite reduction assay on a second said paraffin coated slide to determine the possibility of the presence of MAI on said second paraffin coated slide; and
    after performing said tellurite reduction assay on said second paraffin coated slide and determining that there is a possibility of the presence of MAI on said second paraffin coated slide, performing at least one speciation assay on a third said paraffin coated slide to confirm the presence of MAI on said third paraffin coated slide.

2. The method of claim 1, wherein staining said first paraffin coated slide for alcohol-acid fastness.

3. The method of claim 2, wherein
    said staining step further includes the step of placing said first paraffin coated slide in a tube containing Kinyoun carbolfuchsin;
    immersing said first paraffin coated slide in a tube containing distilled water;
    placing said first paraffin coated slide in a tube containing acid-alcohol;
    immersing said first paraffin coated slide in a tube containing distilled water;
    immersing said first paraffin coated slide in a tube containing an aqueous solution of Methylene blue counterstain; and
    immersing said first paraffin coated slide in a tube containing distilled water.

4. The method of claim 1, wherein
    said tellurite reduction assay includes placing said second paraffin coated slide in a tube containing a sterile aqueous solution;
    adding to said tube a potassium tellurite reagent; and
    determining by the presence or absence of a black precipitate on said second paraffin coated slide after a predetermined time whether MAI is present on said slide.

5. The method of claim 1, wherein a first speciation assay performed on said third paraffin coated slide is a nitrate reduction assay.

6. The method of claim 5, wherein
placing said third paraffin coated slide in a tube containing a sterile aqueous solution containing a nitrate;
removing said third paraffin coated slide from said tube;
adding a reagent to said solution; and
observing said solution to determine the presence or absence of MAI on said third paraffin coated slide.

7. The method of claim 6, wherein
said reagent consists of sulfanilic acid and alpha naphthylamine; and
said solution appears as a red color when nitrate is reduced to nitrite indicating that MAI is not present on said slide.

8. The method of claim 5, wherein
a second said speciation assay performed on a fourth said paraffin coated slide further includes the step of performing a urea hydrolysis reaction assay.

9. The method of claim 8, wherein
placing said fourth paraffin coated slide in a sterile urea broth;
removing said fourth paraffin coated slide from said tube; and
observing said solution to determine the presence or absence of MAI on said fourth paraffin coated slide.

10. The method of claim 9, wherein
said solution appears as a red or pink color indicating that MAI is not present on said fourth paraffin coated slide.

11. The method of claim 8, wherein
a third said speciation assay performed on a fifth said paraffin coated slide further includes the step of performing an emulsifier hydrolysis assay.

12. The method of claim 11, wherein
placing said fifth paraffin coated slide in a sterile broth containing a polyoxyethylene derivative of fatty acid partial esters of sorbitol anhydrides media; and
determining by the presence or absence of a red coloration on said fifth paraffin coated slide after a predetermined time whether MAI is present on said fifth paraffin coated slide.

13. The method of claim 1, wherein
a first said speciation assay performed on said third paraffin coated slide is a nitrate reduction assay.

14. The method of claim 1, wherein
a first said speciation assay performed on said third paraffin coated slide is a further includes the step of performing a urea hydrolysis reaction assay.

15. The method of claim 1, wherein
a first said speciation assay performed on said third paraffin coated slide is an emulsifier hydrolysis assay.

* * * * *